United States Patent [19]
Riegel

[11] Patent Number: 5,493,896
[45] Date of Patent: Feb. 27, 1996

[54] SENSOR ARRANGEMENT FOR DETERMINING GAS COMPONENTS AND/OR GAS CONCENTRATIONS OF GAS MIXTURES

[75] Inventor: Johann Riegel, Bietigheim-Bissingen, Germany

[73] Assignee: Robert Bosch GmbH, Stuttgart, Germany

[21] Appl. No.: 256,941

[22] PCT Filed: Dec. 3, 1993

[86] PCT No.: PCT/DE93/01152

§ 371 Date: Jul. 27, 1994

§ 102(e) Date: Jul. 27, 1994

[87] PCT Pub. No.: WO94/15203

PCT Pub. Date: Jul. 7, 1994

[30] Foreign Application Priority Data

Dec. 23, 1992 [DE] Germany .......................... 42 43 732.6

[51] Int. Cl.[6] .................................................. G01N 27/12
[52] U.S. Cl. .......................................... 73/23.31; 73/31.06
[58] Field of Search ............................... 73/23.31, 23.32, 73/31.05, 31.06; 204/409, 410, 427, 424, 426; 422/94, 95, 96, 97; 338/34

[56] References Cited

U.S. PATENT DOCUMENTS 5,070,721  12/1991  Tantram ........................ 422/94 X

FOREIGN PATENT DOCUMENTS

| | | |
|---|---|---|
| 2284880 | 4/1976 | France . |
| 2603785 | 8/1977 | Germany . |
| 3315654 | 10/1984 | Germany . |
| 2004068 | 3/1979 | United Kingdom . |
| 2208007 | 2/1989 | United Kingdom ............ 73/23.32 |
| 90/10862 | 9/1990 | WIPO . |

OTHER PUBLICATIONS

Database WPI, Week 9116, Derwent Publications Ltd., London, GB; AN 91–115079 & JP–B–3022584 (Toshiba KK), Mar. 27, 1991.

*Primary Examiner*—Hezron E. Williams
*Assistant Examiner*—Michael J. Brook
*Attorney, Agent, or Firm*—Spencer & Frank

[57] ABSTRACT

A sensor arrangement for determining at least one of gas constituents and gas concentrations of a gas mixture including oxidizable gas constituents includes a diffusion duct having a gas mixture gas orifice in communication with the gas mixture and having a reference gas orifice in communication with a reference gas; and a measuring element having a sensitive zone which is positioned in the diffusion duct, the sensitive zone being exposed to the gas mixture via the gas mixture gas orifice and being exposed to the reference gas via the reference gas orifice, wherein the reference gas and the gas mixture have respective oxygen partial pressures, and wherein the oxygen partial pressure of the reference gas is higher than the oxygen partial pressure of the gas mixture so that oxygen is present in the sensitive zone of the measuring element in amounts sufficient to oxidize the oxidizable gas constituents to be measured. In this sensor arrangement, oxygen concentration changes have a negligibly small effect on the sensitive zone and cross-sensitivity of the measuring element with respect to oxygen is largely eliminated.

10 Claims, 1 Drawing Sheet

SENSOR ARRANGEMENT FOR DETERMINING GAS COMPONENTS AND/OR GAS CONCENTRATIONS OF GAS MIXTURES

BACKGROUND OF THE INVENTION

1. Field of the Invention

The invention is based on a sensor arrangement for determining gas components and/or gas concentrations of gas mixtures of the generic type of the main claim.

2. Description of the Related Art

Sensors for determining the content of carbon monoxide in gas mixtures on the basis of semiconducting metal oxides which at high temperatures, as a function of the carbon monoxide content, but also of the oxygen content, change in electroconductivity are known (German Patent 2603785). One metal oxide used is, for example, tin oxide which at elevated temperatures adsorbs oxygen at its surface and ionizes it negatively. As a result, a potential threshold is formed on the grain boundaries of the tin oxide, which threshold grows with increasing concentration of the oxygen adsorbed in ionic form. If the tin oxide surface covered with oxygen then comes into contact with oxidizable gases such as, for example, CO, these are oxidized by the adsorbed oxygen. In the process, the negative charge at the interface and thus the potential threshold is lowered. The surface conductivity of the metal oxide therefore rises again. If the conductivity change is to be utilized for measuring the concentration of oxidizable gas components such as, for example, CO, $NO_x$ and HC, there thus results an oxygen cross sensitivity. In addition, at low oxygen partial pressures and, in particular in association with high temperatures, irreversible reduction of the semi-conducting metal oxide and thus failure of the sensor occurs. Hereinafter, the gas components to be determined are denoted as pollutant components.

SUMMARY OF THE INVENTION

The invention is based on the insight that, if the grain faces of the semiconducting metal oxide are overcrowded with oxygen, even high oxygen concentration changes have a negligibly small effect on the sensitive zone of the measuring element.

The sensor arrangement according to the invention, having the characteristic features of the main claim, has the advantage that by simple means the cross sensitivity of the measuring element with respect to oxygen is largely eliminated. Owing to the simplicity, the sensor arrangement can be fabricated cost-effectively. Moreover, no oxygen pump cell is necessary which pumps oxygen to the measuring element.

As a result of the measures listed in the subordinate claims, advantageous refinements and improvements of the sensor arrangement specified in the main claim are possible. It is particularly advantageous to set, by introducing diffusion barriers, a concentration gradient, sufficiently opposite in direction, of pollutant component and oxygen. If, owing to the exhaust gases of other motor vehicles, a high CO concentration is present in the external air used as the reference gas, an oxidation catalyst is used to oxidize the CO with the air oxygen present in excess. As a result, the CO concentration is reduced to negligible values on the reference gas side, whereas the $O_2$ concentration remains constant, as a first approximation.

BRIEF DESCRIPTION OF THE DRAWINGS

A specific embodiment is described in the invention and shown in more detail in the following description.

DESCRIPTION OF THE PREFERRED EMBODIMENTS

Figure 1:
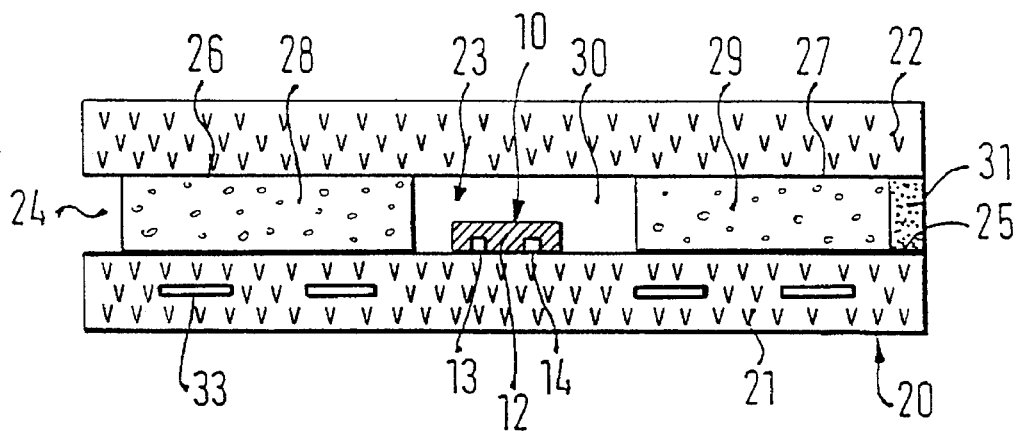
FIG. 1 shows a sectional view of the sensor arrangement according to the invention and FIG. 2 shows the variation of the oxygen and the CO concentration over the length of the diffusion duct according to FIG. 1.

According to FIG. 1, the sensor arrangement consists of a ceramic support 20 made of, for example, $Al_2O_3$, with a bottom ceramic support part 21 and a top ceramic support part 22. Between the ceramic support parts 21, 22 there is a diffusion duct 23 with an exhaust gas-side orifice 24 and a reference gas-side orifice 25. Toward the exhaust gas-side orifice 24 there is formed an exhaust gas-side diffusion section 26, and toward the reference gas-side orifice 25 a reference gas-side diffusion section 27. Inserted in the exhaust gas-side diffusion section 26 there is a porous exhaust gas-side diffusion body 28, and inserted in the reference gas-side diffusion section 27 there is a porous reference gas-side diffusion body 29. Situated between the two diffusion bodies 28, 29 there is a measuring chamber 30. The diffusion duct 23 thus connects the exhaust gas to the external air employed as the reference gas.

Arranged in the measuring chamber 30 there is a measuring element 10 which responds to pollutant components such as CO, $NO_x$ or HC. In the present specific embodiment, a semiconductor gas sensor is used as the measuring element 10. The semiconductor gas sensor has two measuring electrodes 13 and 14, which are overlaid with a semiconducting metal oxide layer 12. The metal oxide layer used in the present specific embodiment for the determination of CO is $SnO_2$. The measuring element 10 in this arrangement is placed, in the diffusion duct 23, on the surface of the bottom ceramic support part 21. The porous shaped bodies 28 and 29 at the same time serve as a protective layer for the metal oxide layer 12 and prevent convection in the diffusion duct 23.

The reference gas-side orifice 25 is sealed, for example with an oxidation catalyst 31. The oxidation catalyst 31 ensures that, in the case of an elevated CO concentration in the external air, the CO is oxidized with the air oxygen present in excess. The CO concentration is thus reduced to negligible values on the reference gas side of the diffusion duct 23. The oxygen concentration, however, remains constant, as a first approximation.

Figure 2:
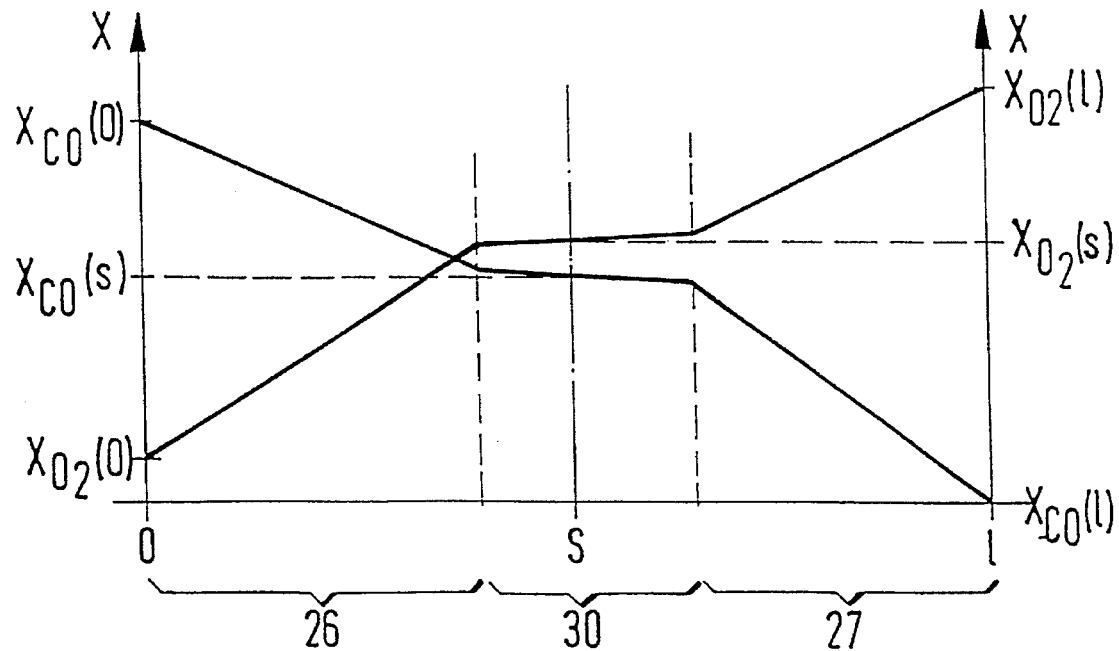

Owing to the concentration conditions of, for example, CO and $O_2$ in the exhaust gas ($XCO=100$ to 8000 ppm, $XO_2<1\%$) and in the external air ($XCO$ negligible, $XO_2=20$ to 21%), the oxygen diffuses from the reference gas-side orifice 25 to the exhaust gas-side orifice 24, and CO from the exhaust gas-side orifice 24 to the reference gas-side orifice 25, as a result of which concentration gradients, of opposite direction, of CO and oxygen are established in the diffusion duct 23 (FIG. 2). This ensures that a sufficiently high oxygen concentration is present in the measuring chamber 30 at the location of the measuring element 10, and the CO concentration behaves proportionately to the CO concentration in the exhaust gas.

The following holds good for the partial pressure of the reducing component, for example CO at the location s of the measuring element 10, with respect to the length 1 of the diffusion duct 23:

$$p\,CO\,(s) = (1 - s/1)\,p\,CO$$

This ensures that the measuring element 10 is at all times exposed to an approximately constant oxygen partial pressure. From the partial pressure of CO at the location of the measuring element 10 it is possible to calculate backwards to obtain the partial pressure of CO in the exhaust gas.

The sensor arrangement has the advantage, in particular, that no extremely narrow tolerances need to be considered when dimensioning the diffusion duct 23. The diffusion duct 23 merely needs to be dimensioned in such a way that the oxygen partial pressure in the measuring cavity 30 is from 0.5 to 20%.

In the present specific embodiment, the bottom ceramic support part 21 contains an integrated heater 33. It is, however, equally conceivable to manufacture the ceramic support 20 from, for example, zirconium oxide. In that case it is necessary, however, to provide an insulating layer, for the measurement element 10, between the ceramic support 20 on the one hand and the measuring electrodes 13, 14 and the metal oxide layer 12 on the other hand. Moreover, in that case, the heater 33 then has to be embedded in an insulating material.

The sensor arrangement is advantageously fabricated in a planar technique by printing, laminating together and sintering of appropriate films, the diffusion duct 23 being formed, for example, by a coating composition being printed which, during sintering, is decomposed, evaporated or burnt without leaving a residue. Alternatively, conceivably, the diffusion duct can be produced by milling or punching a film. The diffusion bodies 28, 29 are generated, for example, by introducing charges composed of porously sintering ceramic materials, e.g., on the basis of $Al_2O_3$ or $ZrO_2$. The diffusion duct 23 further has the measuring element 10 printed into it. An example for the fabrication of a semiconductor gas sensor in planar technique is described in DE-A-2908916.

As far as the mode of operation is concerned, the design principle of the diffusion duct is irrelevant. Equally conceivably, the two diffusion sections 26, 27 may be implemented by holes, for example, in a metal block, and a conventionally constructed gas sensor may be accommodated in a chamber therein.

The use of a heater for setting an appropriate operating temperature depends on the measuring element used. Moreover, it is sufficient for the heater to be integrated into the sensor arrangement only at the location of the measuring element.

What is claimed is:

1. A sensor arrangement for determining at least one of gas constituents and gas concentrations of a gas mixture including oxidizgable gas constituents, comprising:

a diffusion duct having a gas mixture gas orifice in communication with the gas mixture and having a reference gas orifice in communication with a reference gas; and a measuring element having a sensitive zone which is positioned in the diffusion duct, the sensitive zone being exposed to the gas mixture via the gas mixture gas orifice and being exposed to the reference gas via the reference gas orifice, wherein the reference gas and the gas mixture have respective oxygen partial pressures, and wherein the oxygen partial pressure of the reference gas is higher than the oxygen partial pressure of the gas mixture so that oxygen is present in the sensitive zone of the measuring element in an amount which is sufficient to oxidize the oxidizable gas constituents to be measured.

2. The sensor arrangement as claimed in claim 1, further comprising a support, and wherein the measuring element is a semiconductor gas sensor having a plurality of spaced apart measuring electrodes provided on the support and having a semiconducting metal oxide layer which is provided on the plurality of spaced apart measuring electrodes and on the support.

3. The sensor arrangement as claimed in claim 2, wherein the semiconducting metal oxide layer is composed of $SnO_2$.

4. The sensor arrangement as claimed in claim 1, wherein the diffusion duct has a gas mixture gas side diffusion section and a reference gas side diffusion section, wherein the gas mixture gas side diffusion section has inserted therein a porous gas mixture gas side diffusion body, and the reference gas side diffusion section has inserted therein a porous reference gas side diffusion body, and wherein a measuring chamber is defined between the porous gas mixture gas side diffusion body and the porous reference gas side diffusion body, and wherein the measuring element is positioned within the measuring chamber.

5. The sensor arrangement as claimed in claim 4, wherein an oxidation catalyst is provided in the reference gas side diffusion section which is effective to oxidize oxidizable gas constituents contained in the reference gas.

6. The sensor arrangement as claimed in claim 5, wherein the oxidation catalyst is disposed in the reference gas side orifice.

7. The sensor arrangement as claimed in claim 1, further comprising a ceramic support, wherein the diffusion duct is recessed in the ceramic support, and wherein the measuring element is printed on a face within the diffusion duct.

8. The sensor arrangement as claimed in claim 7, wherein the ceramic support is composed of $Al_2O_3$.

9. The sensor arrangement as claimed in claim 7, wherein the ceramic support is composed of $ZrO_2$, and wherein the measuring element is printed, with an insulation layer, onto the face of the diffusion duct.

10. The sensor arrangement as claimed in claim 7, further comprising a ceramic support, wherein the ceramic support has a heater integrally provided therein in an electrically insulating manner.

* * * * *